US006669644B2

(12) United States Patent
Miller

(10) Patent No.: US 6,669,644 B2
(45) Date of Patent: Dec. 30, 2003

(54) MICRO-MACHINED ULTRASONIC TRANSDUCER (MUT) SUBSTRATE THAT LIMITS THE LATERAL PROPAGATION OF ACOUSTIC ENERGY

(75) Inventor: David G. Miller, North Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 7 days.

(21) Appl. No.: 09/919,250

(22) Filed: Jul. 31, 2001

(65) Prior Publication Data

US 2003/0028106 A1 Feb. 6, 2003

(51) Int. Cl.[7] .................................................. A61B 8/14
(52) U.S. Cl. ........................ 600/459; 311/334; 367/181
(58) Field of Search ................................. 600/407, 437, 600/443, 447, 459, 463, 466; 367/181, 153, 157, 173, 174, 175, 180, 163; 216/17, 27; 438/455–465, 689–703, 713; 381/174, 423, 425, 191; 73/625; 29/25.35; 310/314–369

(56) References Cited

U.S. PATENT DOCUMENTS

| | | | | |
|---|---|---|---|---|
| 6,262,946 B1 | * | 7/2001 | Khuri-Yakub et al. | 367/181 |
| 6,430,109 B1 | * | 8/2002 | Khuri-Yakub et al. | 367/181 |
| 6,443,901 B1 | * | 9/2002 | Fraser | 600/459 |

OTHER PUBLICATIONS

Cheng et al., An efficient electrical addressing method using through–wafer vias for two–dimensional ultrasonic arrays, 2000, Ultrasonics Symposium, 2000 IEEE, vol: 2, Page(s): 1179–1182.*

* cited by examiner

*Primary Examiner*—Ali M. Imam
(74) *Attorney, Agent, or Firm*—John Vodopia

(57) ABSTRACT

A micro-machined ultrasonic transducer (MUT) substrate that reduces or eliminates the lateral propagation of acoustic energy includes holes, commonly referred to as vias, formed in the substrate and proximate to a MUT element. The vias in the MUT substrate reduce or eliminate the propagation of acoustic energy traveling laterally in the MUT substrate. The vias can be doped to provide an electrical connection between the MUT element and circuitry present on the surface of an integrated circuit substrate over which the MUT substrate is attached.

11 Claims, 3 Drawing Sheets

MICRO-MACHINED ULTRASONIC TRANSDUCER (MUT) SUBSTRATE THAT LIMITS THE LATERAL PROPAGATION OF ACOUSTIC ENERGY

TECHNICAL FIELD

The present invention relates generally to ultrasonic transducers, and, more particularly, to a micro-machined ultrasonic transducer (MUT) substrate for limiting the lateral propagation of acoustic energy.

BACKGROUND OF THE INVENTION

Ultrasonic transducers have been available for quite some time and are particularly useful for non-invasive medical diagnostic imaging. Ultrasonic transducers are typically formed of either piezoelectric elements or of micro-machined ultrasonic transducer (MUT) elements. The piezoelectric elements typically are made of a piezoelectric ceramic such as lead-zirconate-titanate (abbreviated as PZT), with a plurality of elements being arranged to form a transducer. A MUT is formed using known semiconductor manufacturing techniques resulting in a capacitive ultrasonic transducer cell that comprises, in essence, a flexible membrane supported around its edges over a silicon substrate. The membrane is supported by the substrate and forms a cavity. By applying contact material, in the form of electrodes, to the membrane, or a portion of the membrane, and to the base of the cavity in the silicon substrate, and then by applying appropriate voltage signals to the electrodes, the MUT may be electrically energized to produce an appropriate ultrasonic wave. Similarly, when electrically biased, the membrane of the MUT may be used to receive ultrasonic signals by capturing reflected ultrasonic energy and transforming that energy into movement of the electrically biased membrane, which then generates a receive signal.

The MUT cells are typically fabricated on a suitable substrate material, such as silicon (Si). A plurality of MUT cells are electrically connected forming a MUT element. Typically, many hundreds or thousands of MUT elements comprise an ultrasonic transducer array. The transducer elements in the array may be combined with control circuitry forming a transducer assembly, which is then further assembled into a housing possibly including additional control electronics, in the form of electronic circuit boards, the combination of which forms an ultrasonic probe. This ultrasonic probe, which may include various acoustic matching layers, backing layers, and de-matching layers, may then be used to send and receive ultrasonic signals through body tissue.

Unfortunately, the substrate material on which the MUT elements are formed has a propensity to couple acoustic energy from one MUT element to another. This occurs because the substrate material is typically monolithic in structure and acoustic energy from one MUT element is easily coupled through the substrate to adjoining MUT elements. Therefore it would be desirable to have a way to fabricate a MUT substrate that reduces or eliminates the lateral propagation of acoustic energy.

SUMMARY

The invention is a MUT substrate that reduces or substantially eliminates the lateral propagation of acoustic energy. The MUT substrate includes holes, commonly referred to as vias, formed in the substrate and proximate to a micro-machined ultrasonic transducer (MUT) element. The vias in the MUT substrate reduce or eliminate the propagation of acoustic energy traveling laterally in the MUT substrate. The vias can be doped to provide an electrical connection between the MUT element and circuitry present on the surface of an integrated circuit substrate over which the MUT substrate is attached.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE INVENTION

The invention to be described hereafter is applicable to micro-machined ultrasonic transducer (MUT) elements connected to a substrate on which an integrated circuit (IC) can be formed.

Figure 1:
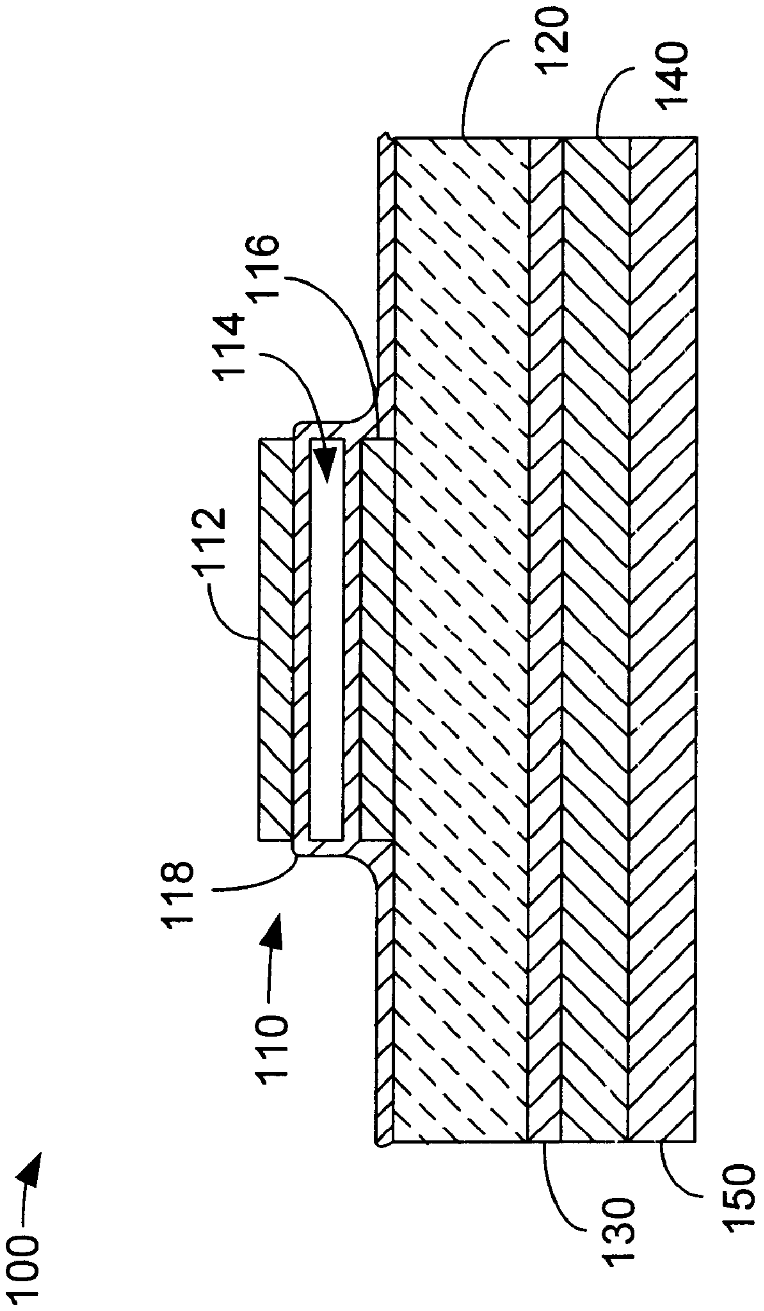
FIG. 1 is a cross-sectional schematic view of an ultrasonic transducer including a MUT element.

FIG. 1 is a simplified cross-sectional schematic view of an ultrasonic transducer 100 including a MUT element. The ultrasonic transducer 100 includes a MUT element 110 formed on the surface of a MUT substrate 120. Preferably, the MUT substrate 120 is silicon, but it can alternatively be any other appropriate material over which a MUT element can be formed. To form the MUT element 110, a conductive layer 116 is formed on a surface of the MUT substrate as shown. The conductive layer 116 can be constructed using, for example, aluminum, gold or doped silicon. A layer of a flexible membrane 118 is deposited over the MUT substrate 120 and the conductive layer 116 so that a gap 114 is formed as shown. The flexible membrane 118 can be constructed using, for example, silicon nitride ($Si_3N_4$) or silicon dioxide ($SiO_2$). The gap 114 can be formed to contain a vacuum or can be formed to contain a gas at atmospheric pressure. A conductive layer 112 is grown over the portion of the flexible membrane 118 that resides over the gap 114, thus forming the MUT element 110.

During a transmit pulse, the flexible membrane 118 deforms in response to electrical stimulus applied to the conductors 112 and 116. The deformation causes acoustic energy to be generated and transmitted both away from the MUT substrate 120 and into the MUT substrate 120. During receive operation, the flexible membrane 118 is electrically biased using electrical stimulus applied through the conductors 112 and 116. When electrically biased, the flexible membrane 118 produces a change in voltage that generates an electrical signal in response to acoustic energy received by the MUT element 110.

The MUT substrate 120 is joined to an integrated circuit (IC) 130 formed on the surface of IC substrate 140. In accordance with an aspect of the invention, the MUT substrate 120 includes a plurality of holes, commonly referred to as vias, formed through the MUT substrate. The vias are formed proximate to the MUT element 110 and reduce or eliminate the lateral propagation of acoustic energy in the MUT substrate 120.

A number of different methodologies can be used to join the MUT substrate 120 to the IC 140, many of which are disclosed in commonly owned assigned U.S. patent application entitled "System For Attaching an Acoustic Element to an Integrated Circuit," filed on even date herewith, and assigned Ser. No. 09/919,470.

A layer of backing 150 can be applied behind the IC substrate 140. The backing 150 acts as an acoustic absorption material. The backing 150 is bonded to the IC substrate 140 using, for example, a bonding material that is preferably acoustically transparent.

Figure 2:
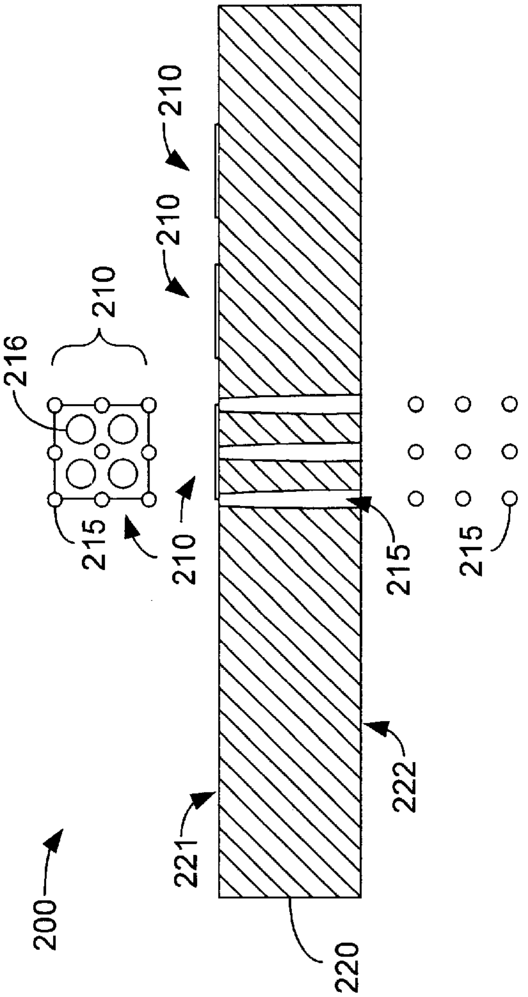
FIG. 2 is a cross-sectional schematic view of a MUT transducer assembly fabricated in accordance with an aspect of the invention.

FIG. 2 is a cross-sectional schematic view of a MUT assembly 200 fabricated in accordance with an aspect of the invention. The MUT assembly 200 includes a MUT substrate 220 upon which a plurality of MUT cells, an exemplar one of which is illustrated using reference number 216, are formed. A plurality of MUT cells 216 form a MUT element 210. In this example, four MUT cells 216 combine to form MUT element 210. The MUT element 210 resides on a major surface of the MUT substrate 220 and is shown exaggerated in profile. In accordance with an aspect of the invention, a plurality of holes, commonly referred to as vias, an exemplar one of which is illustrated using reference numeral 215, are etched through the MUT substrate 220 proximate to each MUT cell 216. For example, as shown in FIG. 2, the four MUT cells 216 are each surrounded by four vias 215. Each via 215 is etched completely through the MUT substrate 220, thereby creating voids in the MUT substrate 220 that reduce or eliminate the propagation of acoustic energy waves traveling laterally through the MUT substrate 220. By reducing these lateral waves, acoustic cross-talk between the MUT elements 210 can be significantly reduced or eliminated.

In another aspect of the invention, each of the vias 215 can be doped to be electrically conductive. By making the vias electrically conductive, circuitry located on the surface of an integrated circuit (not shown in FIG. 2) that is applied to the back surface 222 of the MUT substrate 220 can be electrically connected through the conductive via 215 to each MUT element 210. Although omitted for clarity, each of the vias 215 can be connected to the MUT element 210, thereby creating an electrical connection between the MUT element 210 and the vias 215. In this manner, the vias 215 are used for electrical conduction and to reduce or substantially eliminate acoustic energy traveling laterally in the substrate 220.

The vias can be etched into the MUT substrate 220 from both surfaces 221 and 222. Placing the vias 215 at the respective corners of each MUT element 210 allows the number of MUT cells 216 on the surface 221 to be maximized. Furthermore, as illustrated in FIG. 2, the diameter of the via 215 towards the surface 221 is smaller than the diameter of the via 215 towards the surface 222 of MUT substrate 220. In this manner, the larger diameter portion of the via 215 towards surface 222 can be used to reduce acoustic energy propagating laterally in the MUT substrate 220, while the diameter of the via 215 towards the surface 221 of the MUT substrate 220 can be kept as small as possible. The vias 215 can be etched by using, for example, deep reactive ion etching from the surface 222 to produce a tapered variation in the via diameter as described above. As shown in FIG. 2, the taper of the via 215 is parabolic with the larger diameter towards the surface 222. Furthermore, blind vias or counterbores can also be used to further reduce acoustic energy traveling laterally in the MUT substrate 220.

Figure 3:
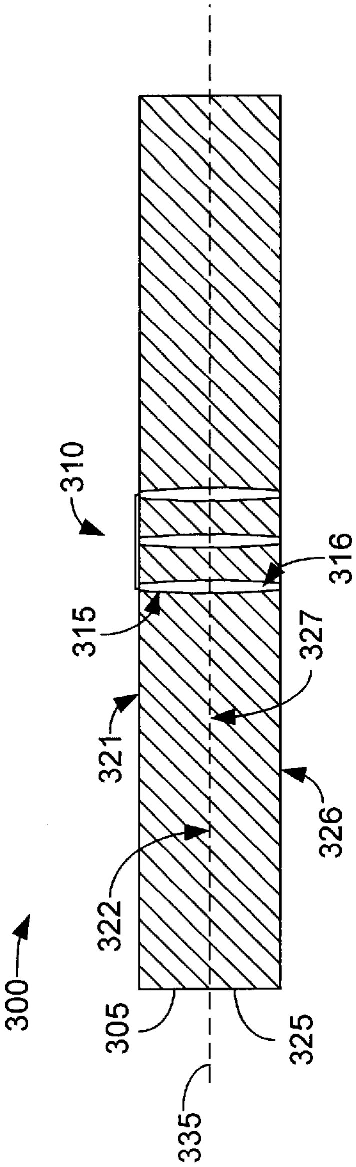
FIG. 3 is a cross-sectional schematic view illustrating an alternative of the MUT transducer assembly of FIG. 2.

FIG. 3 is a cross-sectional schematic view illustrating an alternative of the MUT assembly of FIG. 2. The MUT assembly 300 of FIG. 3 includes a MUT substrate 305 and a MUT substrate 325 bonded "back-to-back" along section line 335. Prior to bonding the two MUT substrates together, the vias 315 are etched into MUT substrate 305 and the vias 316 are etched into MUT substrate 325. By etching the vias into the two thinner substrates 305 and 325, greater precision of the size of the via can be obtained. For example, the vias 315 are etched into the MUT substrate 305 from surfaces 321 and 322. Similarly, the vias 316 are etched into MUT substrate 325 from surfaces 326 and 327. By etching the vias 315 and 316 into two substrates 305 and 325, respectively, each of which are thinner than substrate 220 of FIG. 2, the vias 315 and 316 can be formed with greater precision than the vias 215 of FIG. 2. For example, the position and diameter of each of the vias 315 and 316 can be precisely controlled. Furthermore, the vias 315 and 316 can be tapered as mentioned above.

After the vias are etched, the surface 322 of MUT substrate 305 and the surface 327 of MUT substrate 325 are lapped to reduce the thickness of the substrates 305 and 327 to a desired thickness, and are then bonded together along section line 335. The two MUT substrates 305 and 325 can be anodically bonded, fusion bonded, or brazed together. In this manner, small diameter vias will appear on the surface 321 of MUT substrate 305 and on the surface 326 of MUT substrate 325.

Figure 4:
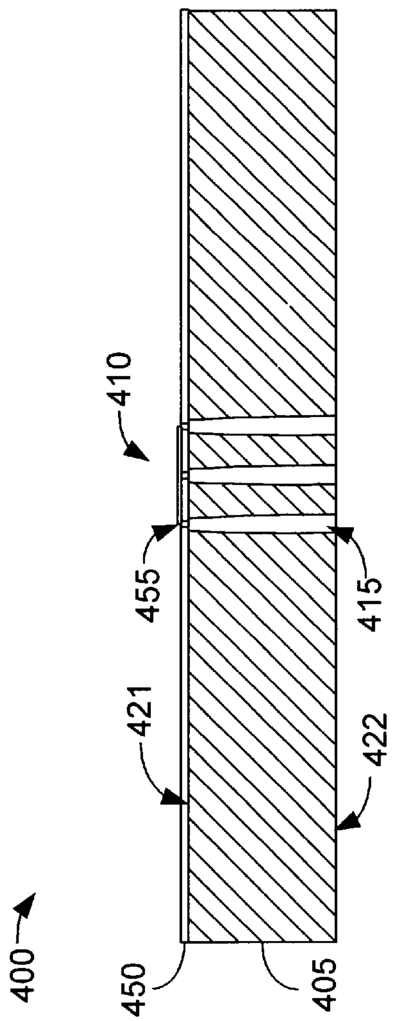
FIG. 4 is a cross-section schematic view of another alternative embodiment of the MUT transducer assembly of FIG. 2.

FIG. 4 is a cross-section schematic view of another alternative embodiment of the MUT assembly 200 of FIG. 2. The MUT assembly 400 of FIG. 4 includes MUT substrate 405, through which vias 415 are etched in similar manner to that described above with respect to FIG. 2. However, the MUT assembly 400 includes an additional substrate 450, which can be fabricated using the same material as MUT substrate 405, bonded to the MUT substrate 405. The MUT element 410 is formed on the additional substrate 450. The additional substrate 450 includes small vias 455 etched through the additional substrate 450 at locations corresponding to the locations of vias 415 in MUT substrate 405. The vias 455 are generally smaller in diameter than the vias 415. In this manner, a greater variation between the size of the via 415 at the surface 422 and the size of the via 455 at the surface 421 can be obtained.

Figure 5:
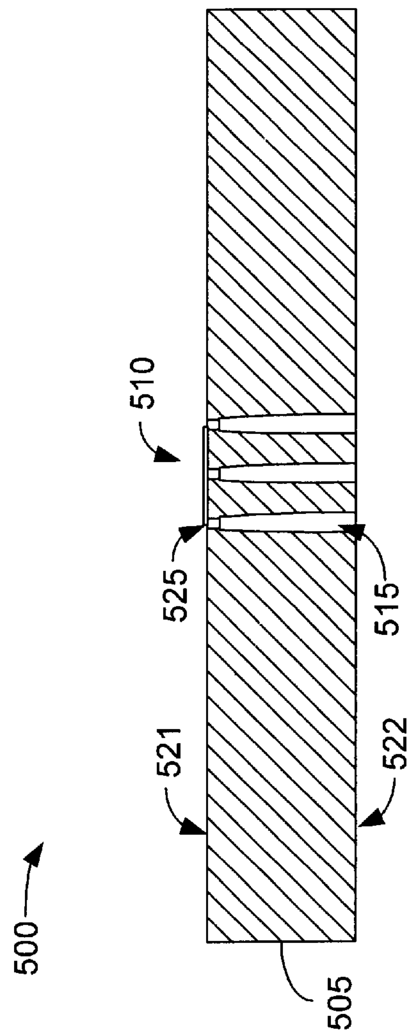
FIG. 5 is another alternative embodiment of the MUT transducer assembly of FIG. 2.

FIG. 5 is another alternative embodiment of the MUT assembly 200 of FIG. 2. The MUT assembly 500 of FIG. 5 includes vias 515 that are etched into MUT substrate 505 from both surface 521 and surface 522. The via portion 525 etched from surface 521 meets the via 515 etched from surface 522 partway through the substrate 505 approximately as shown. Etching the vias from both surfaces 521 and 522 of the MUT substrate 505, enables the diameter of the via to be more precisely controlled.

It will be apparent to those skilled in the art that many modifications and variations may be made to the present invention, as set forth above, without departing substantially from the principles of the present invention. For example, the present invention can be used with MUT transducer elements and a plurality of different substrate materials. All such modifications and variations are intended to be included herein.

What is claimed is:

1. An ultrasonic transducer, comprising:

a plurality of micro-machined ultrasonic transducer (MUT) elements formed on a first substrate, the first substrate including a first surface and, a second surface; and a plurality of vias associated with each MUT element etched into the first and second surfaces of the first substrate and extending entirely through the first substrate, wherein the vias reduce the propagation of acoustic energy traveling laterally in the first substrate, and wherein the vias taper between the first surface of the first substrate and the second surface of the first substrate.

2. An ultrasonic transducer, comprising:

a plurality of micro-machined ultrasonic transducer (MUT) elements formed on a first substrate, the first substrate including a first surface and a second surface; and a plurality of vias associated with each MUT element, where the vias reduce the propagation of acoustic energy traveling laterally in the first, substrate and wherein the first substrate comprises two portions and the vias are etched into each portion so that each via is larger in diameter at the second surface of each portion than at the first surface of each portion.

3. The transducer of claim 2, wherein the second surface of each portion is joined together.

4. The transducer of claim 3, wherein the vias taper in diameter between the first surface and the second surface of the first and second portions.

5. An ultrasonic transducer, comprising:

a plurality of micro-machined ultrasonic transducer (NUT) elements formed on a first substrate, the first substrate including a first surface and a second surface; and a plurality of vias associated with each NUT element, where the vias reduce the propagation of acoustic energy traveling laterally in the first substrate, wherein the vias are etched into the first substrate, and further comprising a second substrate joined to the first substrate and wherein the vias are etched into the second substrate.

6. An ultrasonic transducer, comprising:

a plurality of micro-machined ultrasonic transducer (MUT) elements formed on a first substrate, the first substrate including a first surf ace and a second surface; and a plurality of vias etched into the first substrate and associated with each MUT element, where the vias reduce the propagation of acoustic energy traveling laterally in the first substrate and wherein the vias include a first portion having a first diameter extending from the first surface of the first substrate toward the second surface of the first substrate and a second portion having a varying diameter extending from the second surface of the first substrate toward the first surface of the first substrate.

7. A method of reducing the lateral propagation of acoustic energy in an ultrasonic transducer, the method comprising the steps of:

forming a plurality of micro-machined ultrasonic transducer (MUT) elements on a first substrate, the first substrate including a first surface and a second surface; and forming a plurality of vias proximate to each MUT element through etching the vias into the first surface of the first substrate and the second surface of the first substrate such that the vias extend entirely through the first substrate in order to reduce the propagation of acoustic energy traveling laterally in the first substrate, and further comprising the step of tapering the vias between the first surface of the first substrate and the second surface of the first substrate.

8. A method of reducing the lateral propagation of acoustic energy in an ultrasonic transducer, the method comprising the steps of:

forming a plurality of micro-machined ultrasonic transducer (MUT) elements on a first substrate, the first substrate including a first surface and a second surface; and forming a plurality of vias proximate to each MUT element such that the vias extend entirely through the first substrate in order to reduce the propagation of acoustic energy traveling laterally in the first substrate further comprising the steps of:

forming the first substrate in two portions, each portion including a first surface and a second surface;

etching the vias into each portion so that each via is larger at the second surface of each portion than at the first surface of each portion; and joining the second surface of each portion together.

9. The method of claim 8, further comprising the step of tapering the vias between the first surface and the second surface of the first and second portions.

10. A method of reducing the lateral propagation of acoustic energy in an ultrasonic transducer, the method comprising the steps of:

forming a plurality of micro-machined ultrasonic transducer (MUT) elements on a first substrate, the first substrate including a first surface and a second surface; and forming a plurality of vias proximate to each MUT element by etching the vias into the first substrate such that the vias extend entirely through the first substrate in order to reduce the propagation of acoustic energy traveling laterally in the first substrate further comprising the steps of:

forming a second substrate associated with the first substrate; and etching the vias into the second substrate.

11. A method of reducing the lateral propagation of acoustic energy in an ultrasonic transducer, the method comprising the steps of:

forming a plurality of micro-machined ultrasonic transducer (MUT) elements on a first substrate, the first substrate including a first surface and a second surface; and forming a plurality of vias proximate to each MUT element by etching the vias into the first substrate such that the vias extend entirely through the first substrate in order to reduce the propagation of acoustic energy traveling laterally in the first substrate further comprising the steps of:

forming the vias to include a first portion having a first diameter extending from the first surface of the first substrate toward the second surface of the first substrate; and forming the vias to include a second portion having a varying diameter extending from the second surface of the first substrate toward the first surface of the first substrate.

* * * * *